United States Patent [19]
Evans et al.

[11] Patent Number: 5,439,472
[45] Date of Patent: * Aug. 8, 1995

[54] SURGICAL HANDPIECE CHUCK AND BLADE

[75] Inventors: James A. Evans, Kalamazoo; Gary T. Kalinka, Grand Rapids, both of Mich.

[73] Assignee: Stryker Corporation, Kalamazoo, Mich.

[ * ] Notice: The portion of the term of this patent subsequent to Nov. 23, 2010 has been disclaimed.

[21] Appl. No.: 91,347

[22] Filed: Jul. 14, 1993

Related U.S. Application Data

[63] Continuation of Ser. No. 989,975, Dec. 11, 1992, Pat. No. 5,263,972, which is a continuation of Ser. No. 640,028, Jan. 11, 1991, abandoned.

[51] Int. Cl.⁶ ..................... A61B 17/32; A61B 17/14
[52] U.S. Cl. ...................... 606/176; 606/82; 30/339; 30/351; 83/698.31; 279/102
[58] Field of Search .............. 606/176, 177, 178–180, 606/167–172, 82; 279/76, 96, 101, 102; 83/698.31; 30/335–338, 339, 342, 351, 355, 166.3, 392, 393

[56] References Cited

U.S. PATENT DOCUMENTS

| | | |
|---|---|---|
| 44,823 | 10/1864 | Rose . |
| D. 245,918 | 9/1977 | Shea . |
| D. 294,734 | 3/1988 | Detsch . |
| D. 317,821 | 6/1991 | Aoyagi . |
| 436,804 | 9/1890 | Roberts . |
| 1,048,085 | 12/1912 | MacFarland . |
| 1,064,493 | 6/1913 | Kropat . |
| 1,125,234 | 1/1915 | White . |
| 1,413,101 | 4/1922 | Cushing . |
| 1,448,305 | 3/1923 | Langbein . |
| 1,495,675 | 5/1924 | Colt . |
| 1,808,239 | 12/1927 | Logan . |
| 1,940,855 | 12/1933 | Friedman . |
| 2,557,364 | 6/1951 | Treace . |
| 2,604,130 | 7/1952 | Derby . |
| 2,649,838 | 8/1953 | Krause et al. . |
| 2,854,981 | 10/1958 | Morrison . |
| 3,103,069 | 9/1963 | Gary . |
| 3,542,097 | 11/1970 | Dudek . |
| 3,554,197 | 1/1971 | Dobbie . |
| 3,678,934 | 7/1972 | Warfield et al. . |
| 3,703,036 | 11/1972 | Karubian ............... 30/339 |
| 3,750,283 | 8/1973 | Hoffman . |
| 3,823,473 | 7/1974 | Hoffman . |
| 3,852,881 | 12/1974 | Treace . |
| 3,863,339 | 2/1975 | Reaney et al. . |
| 3,901,117 | 8/1975 | Hoffman . |
| 3,905,105 | 9/1975 | Tuke . |
| 3,905,374 | 9/1975 | Winter . |
| 3,927,893 | 12/1975 | Dillon et al. . |
| 3,943,934 | 3/1976 | Bent . |
| 3,952,412 | 4/1976 | Rhodes . |
| 3,974,868 | 8/1976 | Derbyshire . |
| 3,977,289 | 8/1976 | Tuke . |
| 4,008,720 | 2/1977 | Brinckmann et al. . |
| 4,020,555 | 5/1977 | Hedrick . |
| 4,032,747 | 6/1977 | Kunz . |
| 4,064,871 | 12/1977 | Reno . |
| 4,106,181 | 8/1978 | Mattchen . |
| 4,233,737 | 11/1980 | Poehlmann ............... 30/335 |
| 4,252,121 | 2/1981 | Arnegger . |
| 4,386,609 | 6/1983 | Mongeon ............... 30/339 |
| 4,470,196 | 9/1984 | Hoffman . |
| 4,528,753 | 7/1985 | Kuhlmann et al. . |

(List continued on next page.)

OTHER PUBLICATIONS

Sketch
Stryker Surgical brochure 298-92-16 REV (Mar. 1986).

(List continued on next page.)

Primary Examiner—C. Fred Rosenbaum
Assistant Examiner—Ronald K. Stright, Jr.
Attorney, Agent, or Firm—Flynn, Thiel, Boutell & Tanis

[57] ABSTRACT

A blade with cutting part on one edge portion thereof has a remote end fixed in a chuck by pushing same end-wise into a slot in the chuck through a series of positions, namely (1) drop-out, (2) safety locked-in and (3) fully inserted locked-in.

33 Claims, 4 Drawing Sheets

U.S. PATENT DOCUMENTS

| | | |
|---|---|---|
| 4,584,999 | 4/1986 | Arnegger . |
| 4,617,930 | 10/1986 | Saunders . |
| 4,637,391 | 1/1987 | Schlein . |
| 4,646,440 | 3/1987 | Decker . |
| 4,648,182 | 3/1987 | Hoffman . |
| 4,694,542 | 9/1987 | Koppe . |
| 4,711,030 | 12/1987 | Ruston . |
| 4,730,952 | 3/1988 | Wiley . |
| 4,736,742 | 4/1988 | Alexson et al. . |
| 4,739,557 | 4/1988 | Wagner . |
| 4,768,504 | 9/1988 | Ender . |
| 4,783,886 | 11/1988 | Koppe . |
| 4,819,334 | 4/1989 | Mongeon . |
| 4,891,884 | 1/1990 | Torbet . |
| 4,899,443 | 2/1990 | Beermann . |
| 4,920,646 | 5/1990 | Grant . |
| 5,122,142 | 6/1992 | Pascaloff . |
| 5,133,728 | 7/1992 | Petersen . |
| 5,263,972 | 11/1993 | Evans et al. ............... 606/82 |

OTHER PUBLICATIONS

Copy of Stryker Maintenance Manual entitled "System II OrthoPower 90 Battery Powered Surgical Instruments"—For Use With: 298-92, 94, 96, 98. (Stryker Surgical Brochure 298-92-16 REV (Mar. 1986)).

Aloe Medical Instruments Gallbladder Retractor Item B-1323 p. 115, ©1965.

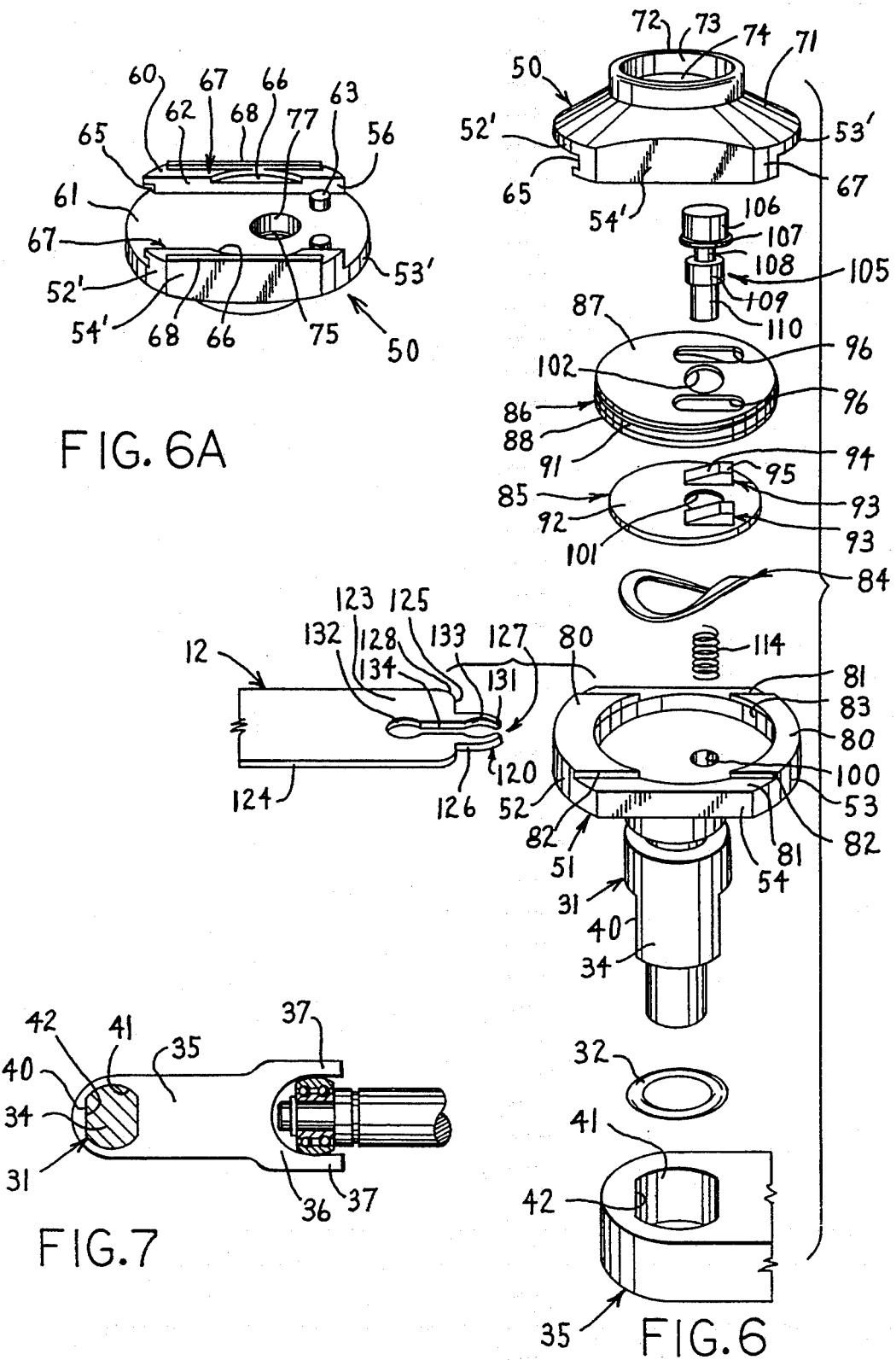

SURGICAL HANDPIECE CHUCK AND BLADE

This is a continuation of Ser. No. 07/989,975, filed Dec. 11, 1992, now U.S. Pat. No. 5,263,972 which in turn is a continuation of Ser. No. 07/640,028, filed Jan. 11, 1991.

FIELD OF THE INVENTION

This invention relates to a cooperating chuck and removable blade for surgical tools, particularly including powered surgical oscillating and sagittal saws.

BACKGROUND OF THE INVENTION

In a prior sagittal saw marketed by the Assignee of the present invention, a powered surgical handpiece carries a sagittal saw chuck capable of removably chucking various blades on a one-at-a-time basis. Each of the prior blades has a widened, rounded base perforated by a coaxially located, circumferentially spaced, pattern of identical through holes and a central, rear opening slit. The prior chuck has a bottom member having a pattern of upstanding pins located to enter the through holes in the blade base. A chuck top member has a center post depending through a central opening of the bottom member and spring biased down to pull the top member down onto the top member's upstanding pins.

To load a blade into the chuck requires gripping of three members as follows.

1. The handpiece is fixedly supported.
2. The resiliently downwardly urged top member is pulled upward from the bottom member pins to open the chuck.
3. The blade base is inserted into the now open chuck with its rear opening slit receiving the top member post.

Chucking of a blade requires that the blade be moved in several directions with respect to the handpiece. More particularly, the blade must be inserted horizontally into the open chuck, then the blade must be pivoted horizontally until its holes align with the upstanding bottom member pins, and then the blade base is dropped onto the chuck bottom member.

Then the spring biased chuck top member can be dropped onto the bottom member pins which then enter into a corresponding pattern of recesses in the bottom of the top member which in turn is pulled down to press down on the base of the blade. In this manner, the blade is locked fixedly with respect to the chuck. Removal of a blade from the chuck involves a reversal of the aforementioned steps.

Although the above-described prior chuck and tool have worked well for a substantial period of time, and have been found satisfactory by surgeons, nevertheless, the present Applicant has noted certain drawbacks of the above-discussed prior system, which drawbacks the present invention is intended to cure.

Accordingly, the objects and purposes of the present invention include provision of a surgical tool chuck and blade structure in which full insertion of blade into chuck can be done easily with only two (rather than three) hands; in which a blade is chucked merely by pushing it longitudinally into the chuck while pushing a locking element on the chuck; in which the blade is either obviously insufficiently inserted or is positively locked against escape from the chuck; in which significant insertion of the blade into the chuck requires manual pushing of a locking element; in which such insufficient insertion is made obvious by a number of observables including short insertion distance before insertion is positively blocked, virtually no blade retention force, free pivoting of the blade from side to side and up and down (roll and pitch) with respect to the chuck, and dropping of the blade out of the chuck upon almost any movement of the chuck or handpiece; in which positive locking of the blade in the chuck is present for almost the entire longitudinal insertion of the blade base into the chuck; in which such positive locking prevents the blade from accidentally being removed from the chuck even when the blade is not fully inserted into the chuck; in which the possibility of accidental release of the locking element by careless handling of the chuck or handpiece is minimized; in which a blade can simply be dropped out of its fully inserted and positively locked position in the chuck by one handed gripping of the chuck in a way to push the locking element; in which the blade tends to be seated more firmly in the chuck during cutting; in which locking of the blade in the chuck and prevention of rocking of the blade in the chuck are carried out by different portions of the chuck acting on the blade; in which the chuck can be made more compact than the prior chuck above described, in which the chuck and blade are of simple relatively inexpensive construction, in which blades of a range of differing thicknesses can be inserted in the chuck without any manipulation of the chuck to compensate for differences in thickness and wherein the chuck automatically compensates for differences in thicknesses of blades; in which the number of parts is substantially reduced; in which the blade receiving portion of the chuck is constructible in two facing pieces which can be easily machined and thereafter permanently fixed together as by electron beam welding, and in which the insertion and removal of a blade with respect to the chuck can be carried out by persons without special training and under the adverse conditions often encountered in surgery.

Further objects and purposes of the invention will be apparent to persons familiar with an apparatus of this kind upon reading the following description and upon inspection of the accompanying drawings.

SUMMARY OF THE INVENTION

A blade with cutting means on one edge portion thereof has a remote end fixed in a chuck by pushing same end-wise into a slot in the chuck through a series of positions, namely (1) drop-out, (2) safety locked-in and (3) fully inserted locked-in.

BRIEF DESCRIPTION OF THE DRAWINGS

FIG. 6 is an exploded pictorial view of the FIG. 1 chuck.

FIG. 6A is a pictorial view of the chuck top member of FIG. 6 but oriented upside down (as if rotated from FIG. 6 about a horizontal axis in the plane of the page).

FIG. 7 is a fragmentary sectional view taken substantially on the line 7—7 of FIG. 2.

DETAILED DESCRIPTION

Figure 1:
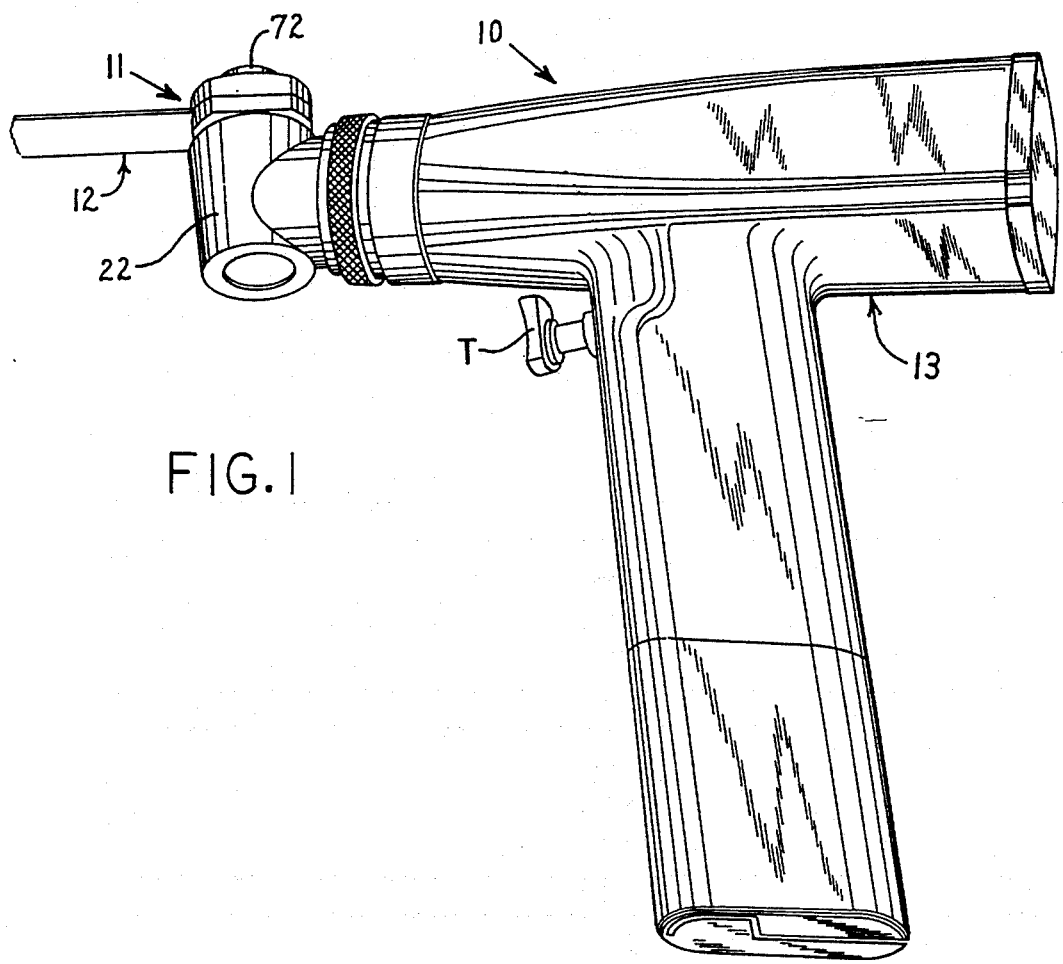
FIG. 1 is a pictorial view of a surgical handpiece of a kind usable as a powered sagittal or oscillating saw, and including a chuck and blade construction embodying the present invention.

FIG. 1 discloses a powered surgical handpiece 10 which provides a typical environment for a chuck 11 and blade 12 more specifically embodying the invention. The handpiece 10 may be of the type including a housing 13 enclosing a motorized drive assembly 14 of any convenient type schematically indicated in FIG. 2. The motorized drive assembly 14 typically includes a drive motor M powered from a power source P through a switch S in turn actuated by a trigger T. In one embodiment according to the invention, the power source P is electric, although other energy sources (for example, compressed air) are contemplated.

Figure 2:
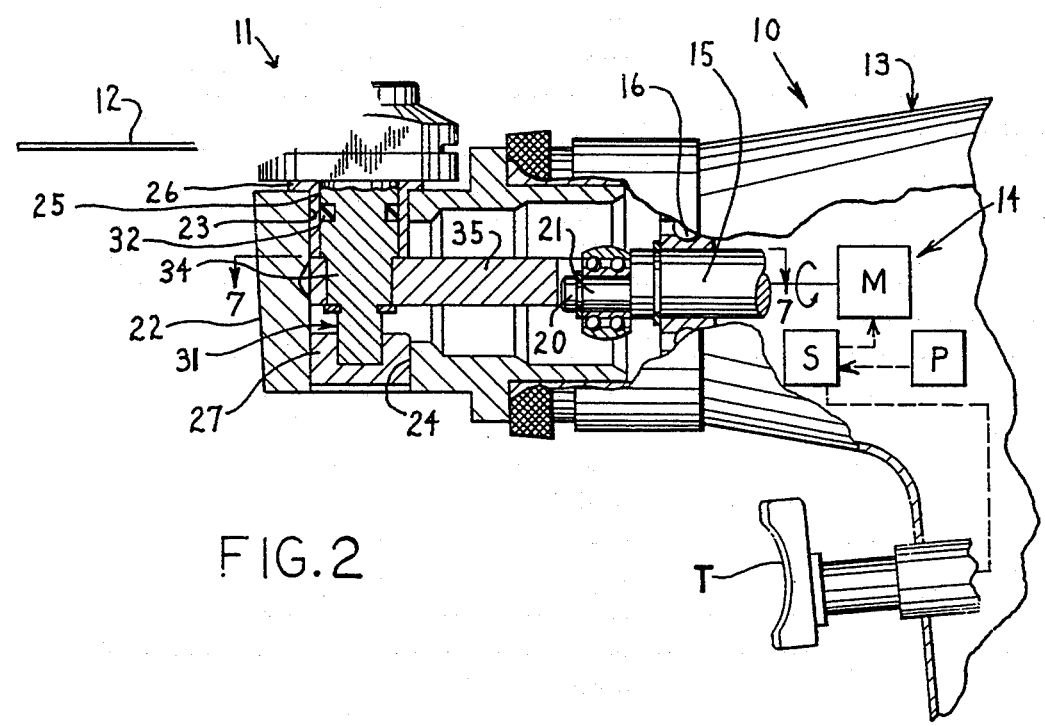
FIG. 2 is an enlarged central cross-sectional view, in elevation, of a fragment of FIG. 1 handpiece showing a chuck and blade embodying the invention and a drive structure therefor, as supported in a forward portion of the handpiece of FIG. 1.

Although oscillating motion about a vertical axis (in FIG. 2) may be imparted to the chuck 11 by any convenient means, in the example shown in FIG. 2, the motor M drives a rotatable shaft 15, rotatably supported by suitable bearings, as at 16, supported by the housing 13. The forward end of the shaft 15 carries an axially extending but eccentrically located drive pin 20 fixed thereon and in turn carrying a bearing 21 axially fixed thereon.

Fixed to and extending forward from the housing 13 is a hollow extension 22, which is blind at its forward end but has coaxially spaced top and bottom through bores 23 and 24. An axial sleeve 25 is press fitted down into the top bore 23 and has a radial flange 26 resting atop the extension 22. A blind bottomed bushing 27 is press fitted up into the bottom bore 24 coaxially of the sleeve 25.

The chuck 11 includes a central depending shaft 31 supported for pivotal movement about its longitudinal axis (vertical in FIG. 2) by the sleeve 25 and bushing 27. In the embodiment shown, the shaft 31 has maximum and minimum diameter portions at the top and bottom thereof which are respectively rotatably supported by the sleeve 25 and bushing 27. The maximum diameter portion of the shaft is annularly grooved to receive an O-ring 32 (FIG. 2) which seals against the sleeve 25. The O-ring 32 and blind bushing 27 seal the interior of the housing extension 22.

An intermediate portion 34 of the shaft 31 disposed just below the sleeve 25 has fixed thereto the forward (leftward) end of a link 35. The rearward (rightward) end of the link 35 forms a fork 36 (FIG. 7). The fork 36 has a laterally spaced pair of rearwardly extending tines 37. The tines 37 snugly receive laterally therebetween the outer race of the bearing 21 carried by the eccentric drive pin 20. The opposed surfaces of the tines 37 are vertical and extend above and below the central axis of the rotating shaft 15 sufficiently to maintain contact with the outer race of the bearing 21 as it moves on a vertical plane, through the circular orbit of the eccentric pin 20, as the pin orbits in response to rotation of the shaft 15. Thus, as the shaft 15 rotates and the eccentric pin 20 and surrounding bearing 21 orbit, the bearing 21 moves up and down along the opposed faces of the tines 37 in response to the vertical component of the orbit and pivotally rocks the fork 36 and link 35 and chuck 11 about the vertical axis of the chuck shaft 31 in response to the horizontal component of the orbit. Such rocking thus is in a horizontal plane and more specifically in a direction into and out of the page in FIG. 2 and is in the plane of the page in FIG. 3. Such pivotal rocking of the chuck 11, causes a blade 12 carried by the chuck 11 to oscillate horizontally.

To assure that the link 35 positively oscillates the chuck shaft 31, the chuck shaft 31 (FIG. 7) in its intermediate portion 34 may be provided with oppositely facing flats 40. The forward end of the link 35 receives the intermediate portion 34 of the shaft 31 in a broached, vertical, through hole 41 provided with corresponding flats 42. The hole 41 in the forward end of the link 35 is thus sized and shaped to receive the intermediate portion 34 of the shaft 31 vertically therethrough in fixed, press fitted, and positive driving relation.

To the extent above described, the apparatus is conventional and is disclosed as a typical environment for the chuck 11 and blade 12 more specifically embodying the invention.

It will be noted that variations on the above-described environmental apparatus are contemplated. For example, the desired oscillating motion may be imparted to the chuck 11 and blade 12 by other means than the link 35 and orbiting eccentric 20 discussed above, although the disclosed link and eccentric structure discussed above provide an effective yet economical structure for imparting the desired oscillatory movement to the chuck 11 and blade 12.

Figure 4A:
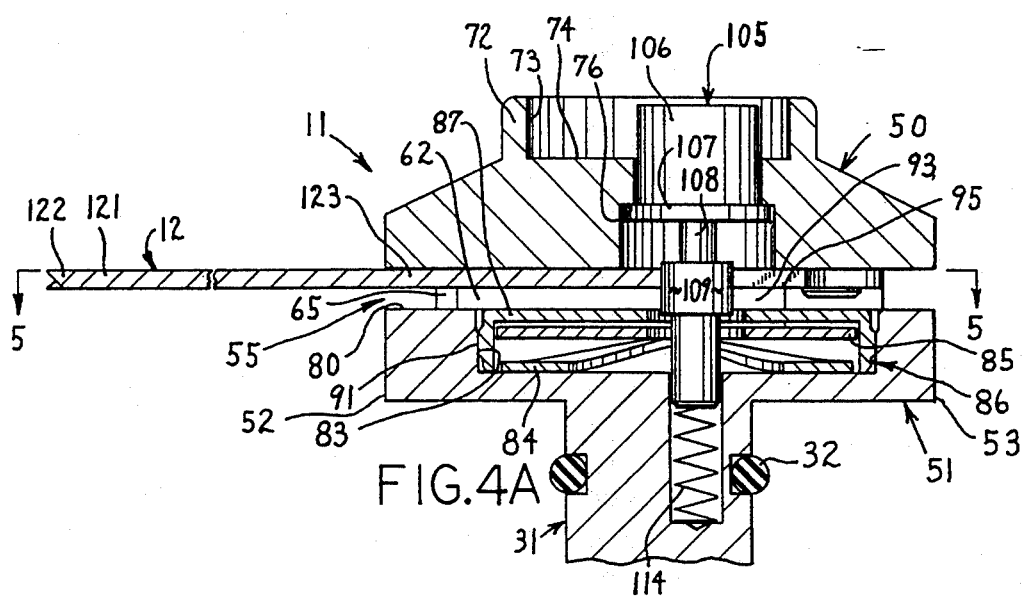
FIGS. 4 and 4A are enlarged central cross-sectional views substantially taken on the line 4A—4A of FIG. 3 and respectively showing partly and fully inserted blade positions corresponding to FIGS. 5D and 5E.
Figure 4:
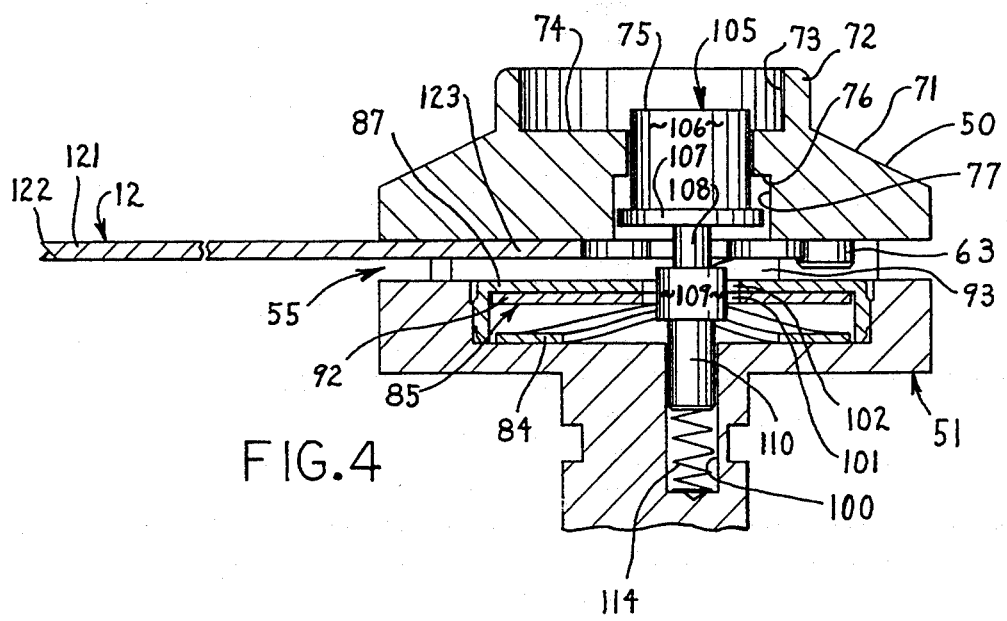

Turning now to structure more directly embodying the invention, the chuck 11 comprises facing top and bottom casing members 50 and 51 (FIGS. 4 and 6). The bottom casing member 51 is fixed centrally atop, and preferably integral with, the shaft 31. In the embodiment shown, the casing members 50 and 51 have the same outline in top plan view. In the bottom member 51, the forward and rearward ends 52 and 53 (FIG. 6) respectively are convexly rounded and connected by longitudinal sides 54 which are flatted and parallel. As seen at 52'-54', the top member 50 is similar.

The chuck 11 has a horizontal, longitudinal, preferably rectangular cross section, forward opening slot 55 (FIG. 4) in which the rear end portion of the blade 12 is received as hereafter discussed. The slot 55 is formed by a corresponding longitudinal, rectangular cross section groove 56 (FIG. 6A) extending centrally in the bottom face 60 of the top member 50. The groove 56 opens through the front end 52' of the top member 50. The groove 56 may open through the rear end 53' for convenience in machining. The groove 56 has side walls 62 connected by a central flat 61 depressed from but parallel to the plane of the bottom face 60. The side walls 62 of the groove 56 are parallel and extend forwardly/rearwardly of the top chuck member 50 and here are perpendicular to the groove central flat 61 and the bottom face 60.

Two projections, here pins 63 (FIG. 6A), fixedly depend from the central flat 61 near the rear end 53' of top member 50 and are spaced between the groove side walls 62 and the front rear center line of the top member 50. The pins 63 may readily be fixed to the top member 50 by press fitting into vertical blind holes (not shown) in the top member 50. The pins 63 extend about half the depth of the slot 55 (FIG. 4A).

The front edges 65 (FIG. 6A) of the side walls 62 of the groove 56 in the top member 50 are rounded or bevelled to facilitate entry of the blade 12 into the slot 55 defined by the groove 56 and to reduce subsequent stress of the blade 12 bearing thereupon. The bottom face 60 of the top member 50 has laterally opposed, semicircular notches 66 which open toward each other across the groove 56, through the respective groove side walls 62, and extend vertically partway the depth of the groove side walls 62. The laterally opposed notches 66 are here offset slightly to the rear along the groove 56 but are forward of the pins 63. The notches 66 define diametrally opposed chordal portions of an imaginary circle laterally centered on the top member 50.

The groove 56 may be thought to define a laterally opposed pair of side bulkheads 67 (FIG. 6A). The side bulkheads 67 thus are flush with the sides 54' of the top member 50 and define the bottom face 60 and side walls 62. The bevels 65 and notches 66 are in the side bulkheads 67.

In the embodiment shown, a sacrificial ridge 68 (FIG. 6A) depends from the bulkheads 67 on each side of the top member 50. Each ridge 68 is flush with the corresponding outer side 54' of the top member 50 and extends the front-rear length thereof. The ridges 68 here extend along the outside perimeter of the respective notches 66. The ridges 68 are here of substantially rectangular cross section. The cross section of the ridges 68 is very small compared to the cross section of the corresponding bulkheads 67. The ridges 68 are sized to melt down during electron beam welding of the top member 50 to the bottom member 51 to weld the same together face to face.

In the embodiment shown, the top 71 (FIG. 6) of the top member 50 tapers upward toward an upstanding, cylindrical, circular fence 72 (FIG. 6). The fence 72 surrounds an upward facing recess 73 having a flat bottom 74 (FIGS. 6 and 4). In the embodiment shown, the fence 72 is substantially centered atop the top member 50. A vertical hole 75 extends down through the top member 50, as seen in FIGS. 4 and 6A. The hole 75 is centered laterally between the bulkheads 67 but is offset somewhat rearwardly on the top member 50. The hole 75 indeed has its center somewhat rearward of the center of the notches 66 but forward of the pins 63.

The bottom portion of the hole 75 is enlarged in diameter to form a downward facing step 76 (FIG. 4) and a corresponding downward opening recess 77. The recess 77 opens through the central flat 61 of the top member 50. The top of the hole 75 opens through the flat bottom 74 of the upward facing recess 73 bounded by the fence 72 and is offset rearwardly in the recess 73.

Figure 9:
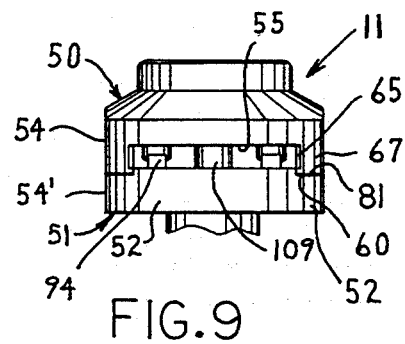
FIG. 9 is a front elevational view of the chuck of FIG. 8, with no blade inserted.

The bottom member 51 has a top face 80 (FIG. 6) in a plane perpendicular to the longitudinal axis of the shaft 31, and hence oriented horizontally in FIG. 6. The top face 80 is laterally flanked by coplanar flats 81 which extend forward-rearward along the respective sides 54 of the bottom member 51. The flats 81 are offset downward from the plane of the top face 80 by laterally outward facing steps 82. The height of the steps 82 is less than the height of the side walls 62 of the bulkheads 67 of the top member 50, by an amount corresponding to the height of the blade receiving slot 65 (FIG. 9) of the chuck 11. The flats 81 are horizontally sized to snugly receive thereon the respective bulkheads 67 of the top member 50 as seen for example in FIG. 9. This prevents lateral movement of the top member 50 with respect to the bottom member 51 during electron beam welding together of the members 50 and 51. During electron beam welding, the meltdown of the ridges 68 on the top member 50 results in face-to-face engagement of the bottom face 60 (the bottom of the bulkheads 67) of the top member 50 with the upward facing flats 81 of the bottom member 51 as seen in FIG. 9.

A shallow, circular, cylindrical recess 83 is sunk in the top face 80 of the bottom member 51 and is slightly offset to the rear therein as seen in FIG. 6. The laterally opposed, semicircular notches 66 in the underside of the bulkheads 67 of the top member 50 over-lie the laterally opposed portions of the recess 83 in the bottom member 51, which portions extend laterally into the flats 81 of the bottom member 51. Thus, the semicircular notches 66 accommodate laterally opposed top portions of the shoe cover 86, in the assembled chuck 11. The recess 83 and flats 81 leave the top face 80 in the form of two semi-circular upward facing surfaces of which the front is somewhat wider in a frontrear direction than the rear.

The recess 83 contains, in ascending order, a compression spring in the form of a resilient wave washer 84 (FIGS. 4A and 6), a disk-like shoe 85, and an inverted cup-shaped shoe cover 86.

The cup-shaped shoe cover 86 has a flat top end wall 87 (FIGS. 6) of circular shape from which depends an annular peripheral wall 88. The height of the shoe cover 86 corresponds to the depth of the recess 83. The shoe cover 86 is press fitted fixedly into the recess 83, its top wall 87 flush with the top face 80 of the bottom member 51. The bottom of the peripheral wall 88 may rest on the bottom of the recess 83. To facilitate press fitting of the shoe cover 86 into the recess 83, the peripheral wall 88 of the shoe cover is on its outer face provided with an axially and radially narrow annular ridge 91 which snugly engages the side wall of the recess 83 in press fit relation therewith. The shoe cover 86 and the bottom of the recess 83 define a chamber in which the wave washer 84 and the overlying shoe 85 are housed in radial clearance, vertically movable relation. The wave washer 84 resiliently presses the shoe 85 upward against the top end wall 87 of the shoe cover 86 as shown in FIG. 4.

The shoe 85 comprises a circular disk 92 (FIG. 6) fixedly supporting a laterally spaced pair of ramps 93. The ramps 93 are offset somewhat to the rear on the upper face of the disk 92 and are laterally spaced on opposite sides of the front-rear centerline of the disk. The ramps 93 are preferably identical and each has a relatively shallow, forward facing and downward extending slope 94 which occupies most of the length of the ramp 93, and a relatively short, horizontal top 95.

The top wall 87 of the shoe cover 86 is pierced by laterally spaced, forward-rearward extended slots 96 (FIG. 6) sized and located to allow the ramps 93 to extend upward therethrough with sufficient horizontal clearance as to allow the disk 92 of the shoe 85 to move up and down within the shoe cover 86. The outside diameter of the disk 92 is slightly less than the inside diameter of the shoe cover peripheral wall 88, so as not to restrict such up and down movement. Different vertical positions of the shoe 85 under the top 87 of the shoe cover 86 are seen for example in FIGS. 4 and 4A, and in FIGS. 4B and 4C. In their uppermost position (for example in FIG. 4B), the ramps 93 extend almost up to the central flat 61 of the upper member 50, being spaced therefrom by less than the thickness of the thinnest blade 12 intended to be chucked in the chuck 11.

Figure 5A:
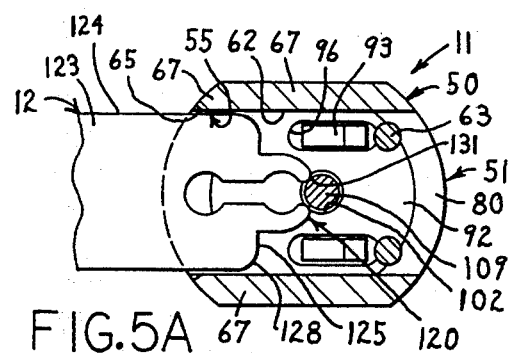
FIGS. 5A-5E are corresponding reduced cross-sectional views substantially taken on the line 5—5 of FIG. 4A with the blade at successive positions of insertion in the chuck.

As seen in FIG. 5A, the depending pins 63 of the top member 50 are each forward-rearward aligned with a corresponding ramp 93 and slot 96.

The bottom of the recess 83 (FIGS. 4 and 6), the disk 92, and the shoe cover top wall 87 have coaxially aligned holes 100, 101 and 102 respectively. The holes 100-102 are offset somewhat rearward on their respective members and are all in coaxial alignment with the hole 75 and recess 77 in the top member 50. In the embodiment shown, the holes 101 and 102 are of diameter less than the hole 75 but of diameter greater than the hole 100. The holes 101 and 102 are through holes. The hole 100, although axially much longer (deeper) than the holes 101 and 102, is blind as seen in FIG. 4.

The holes 100-102 are offset somewhat rearward of the central axis of the shaft 31, and are located laterally between the ramps 93, slots 96 laterally and forward of the pins 63.

A locking spindle 105 (FIGS. 4 and 6) comprises, in sequence downwardly, an enlarged cylindrical head 106, a radially outward extending flange 107, an unlocking segment 108 of substantially reduced diameter, a locking segment 109 of intermediate diameter, and a shank 110. The shank 110 is here of diameter between that of the segments 108 and 109. The elements 106-110 are coaxial and preferably are all cylindrical and of circular cross section.

A coil compression spring 114 is received with clearance in the blind hole 100 and can expand and be compressed axially in such hole 100. The shank 110 is snugly but vertically slidably received in the hole 100 atop the spring 114. The holes 101 and 102 in the shoe 85 and shoe cover 86 are sized to receive loosely therethrough the segments 108 and 109 and the shank 110 of the locking spindle 105, as seen in FIG. 4. The head 106 and flange 107 of the locking spindle 105 substantially exceed the diameter of the holes 101 and 102. However, the head 106 and flange 107 are of diameter to be snugly but vertically slidably received in the hole 75 and recess 77 in the top member 50.

The flange 107 (FIG. 4A) is of diameter larger than the hole 75 so as to coact with the step 76 to prevent the locking spindle 105 from escaping upward through the top member 50, despite the upward urging of the partially compressed compression spring 114. In other words, the flange 107 traps the locking spindle 105 within the chuck 11. In particular, the locking spindle 105 is free to move up and down in the chuck 11 until the flange 107 collides with either the step 76 or the top end wall 87 of the shoe cover 86 (assuming no blade 12 is in place in the chuck).

In its uppermost position, the top of the spindle head 106 is spaced slightly below the top of the fence 72 (FIG. 4A). In this uppermost position, the top of the locking spindle head 106 spaced well above the bottom 74 of the recess 73 defined by the fence 72. In this way, the fence 72 and spindle head 106 cooperate to allow intended pushing down of the locking spindle 105, from its FIG. 4A position toward its FIG. 4 position, by use of a thumb or finger, but to prevent accidental (unintended) pushing down of the locking spindle 105 when the palm of the user is pressed against the top of the chuck 11, as when a surgical assistant passes the handpiece 10 to a surgeon while grasping it by means of the chuck.

The blades 12 (FIG. 3) to be used with the chuck 11 include a cutting portion 121 remote from the chuck and typically being formed as a set of cutting teeth 122. Further, the blades 12 each have a mounting portion 123 (FIGS. 4 and 5A) to be received in the chuck 11. While the blades useable with the chuck 11 may take a variety of forms, in accord with their particular cutting task, and may thus differ in their size and shape outside the mounting portion 123 thereof, and indeed may even differ in the thickness of the mounting portion 123 thereof, up to a maximum thickness which can be received in the chuck slot 55, a typical blade 12 is here shown for purposes of illustration. The typical blade 12 here shown is of flat metal (preferably the relatively hard grade of stainless steel typically used for surgical saw blades), and is of elongate, generally rectangular plan, with the teeth 122 at the forward end thereof and the mounting portion 123 at the rearward end thereof.

Figure 5B:
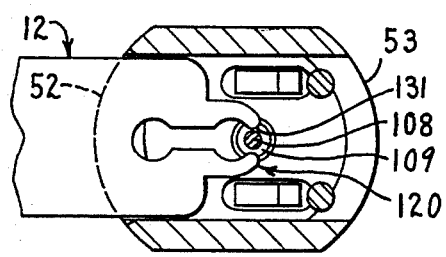
Figure 5C:
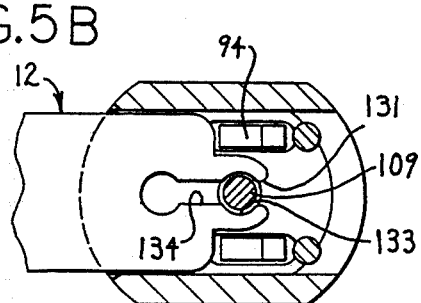
Figure 5D:
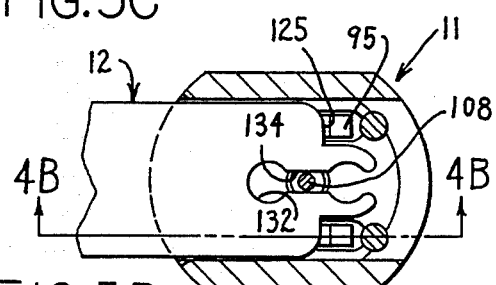
Figure 5E:
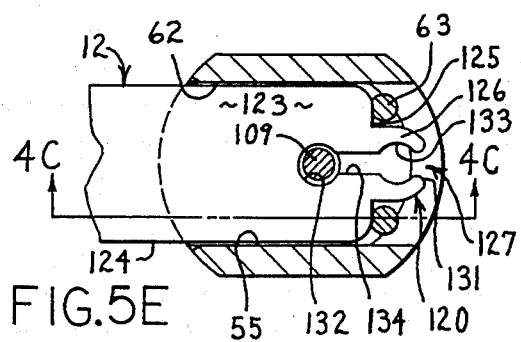

The mounting portion 123 of the blade 12 comprises parallel opposed side edges 124 (FIG. 5A) snugly but slidably received between the side walls 62 of the slot 55. It is desirable that, as seen in FIG. 5E, the width of the blade mounting portion 123 is very nearly as great as the width of the slot 55 into which it is rearwardly slidably receivable. It is also desirable that the side edges 124 be long, e.g. nearly as long as the slot 55. This snug but slidable contact over most of the length of the groove 56 prevents rocking of the blade 12 from side to side with respect to the chuck 11 during cutting, so that when the chuck 11 oscillates, horizontally, such motion is imparted to a blade 12 therein.

The rear end 125 of the blade meets the side edges 124 at rounded or beveled corners 128 (FIG. 5A) to ease insertion of the blade 12 rearwardly into the slot 55.

Integral with and extending rearward from the rear end 125 of the blade is rounded end nose 120 (FIGS. 5E and 6) centrally divided into a pair of laterally close-spaced nose means, or tines, 126 spaced by a narrow central slit 127. The nose 120 is narrow compared to the width of the blade 12. The nose 120 is longitudinally short compared to the width of the mounting portion 93 of the blade 12. The slit 127 is of dumbbell shape, having an opposed pair of front notches and an opposed pair of rear notches here defined by respective circular front and rear parts 132 and 133, connected by a laterally narrower but longer neck 134. The front and rear parts 132 and 133 respectively comprise second and first widenings of the slit 127. The widening 133 defines opposed first and second safety locking means (defined by said opposed rear notches) and the widening 132 defines opposed first and second final locking means (defined by said front notches), the locking means here being formed by the above-mentioned notches. The open rear mouth 131 of the slit 127 is bevelled or rounded. The mouth 131 and neck 134 are sized to pass therethrough the unlocking segment 108 of the spindle 105 but not the locking segment 108, as seen in FIGS. 5B and 5D. Conversely, the circular parts 132 and 133 are sized to snugly receive the locking spindle 109 of the spindle 105 as seen in FIGS. 5C and 5E therein. Alternatively, it is convenient to note, in geographic terms, that the slit 127 is bounded along one side edge by a safety peninsula at the mouth 131, a locking peninsula at the neck 134, a first bay at the rear slit part 133 and a second bay at the front slit part 132, wherein such one slit side edge may be termed a mounting edge comprising such safety peninsula, first bay, locking peninsula and second bay. Across the slit 127 is the opposite slit edge (second mounting edge) wherein the opposed locking peninsula may be said to define a final lock means and the opposed safety peninsulas a safety lock means.

OPERATION

The blades 12 may be formed conventionally from stainless steel sheet stock, for example, by stamping and setting and hardening the teeth.

The parts of the chuck 11 are machined, or otherwise formed in any convenient manner, preferably from stainless steel stock. The resulting chuck parts shown in FIG. 6 are then assembled. More particularly, and most easily with the parts turned upside down, the shoe 85 and wave washer 84 are placed in the open end of the shoe cover 86 with the ramps 93 extending through the slots 96. The thus loaded shoe cover 86 has its peripheral wall 88 press fitted into the recess 83 in the bottom member 51. This traps the wave washer and shoe 85 between the top end wall 87 of the shoe cover and the bottom of the recess 83 in the bottom member 51, as seen for example in FIG. 4. The resultant assembly can then be turned to the upright position shown in the drawings.

The coil spring 114 and the shank 110 of the spindle 105 can then be dropped down through the holes 101 and 102 (FIG. 4) and into the blind hole 100 in the bottom member 51. The chuck top member 50, with its fixed dependent pins 63, can then be placed atop the bottom member 51, while the hole 75 and recess 77 in the top member 51 respectively receive the head 106 and flange 107 of the spindle 105. With the top and bottom members 50 and 51 properly aligned, electron beam welding melts down the sacrificial ridges 68 in the top member 50 to weld the top member bulkheads 67 atop the bottom member flats 81 (FIGS. 6 and 9). This completes assembly of the chuck 11 in its condition of FIGS. 4A and 9). The top and bottom members 50 and 51 thus become a one-piece unit and define the rectangular cross section, blade receiving slot 55 (FIGS. 4 and 9).

The assembled chuck 11 can then be pivotally mounted on the extension 22 on the front end of the handpiece 10. More particularly, with the sleeve 25 (FIG. 2) fixed in the top bore 23 of the extension 22, the chuck shaft 31 is slid downward through the sleeve 45 until the chuck bottom member 51 seats firmly on the flange 26 and the intermediate portion 34 is located below the sleeve 25.

The link 35 is predisposed in the hollow interior of the extension 22. As the chuck 11 is moved downward toward the extension 22 and the chuck shaft 31 slides downward through the sleeve 25, the lower end of the shaft 31 is guided through the hole 41 in the forward end of the link 35. A conventional tubular mandrel not shown can be inserted upward through the open bottom bore 24 to receive the bottom end of the shaft 31 and press the forward end of the link 35 onto the intermediate portion 34 of the shaft 31, with the flats 42 and 40 of the link 35 and shaft intermediate portion 34 opposed. The mandrel can then be withdrawn and the blind bushing 27 pressed upward into the bore 24 and over the bottom portion of the shaft.

It is desirable that foreign material from outside the handpiece be prevented from entering along the chuck shaft 31 into the interior of the extension 22. Thus, in the embodiment shown, the groove in the upper portion of the chuck shaft 31 is provided with a suitable seal, such as O-ring 32 to bear against the interior surface of the sleeve 25 and effect a seal thereagainst while allowing horizontal pivoting of the chuck 11. Similarly, at the bottom of the shaft 31 the closed end bushing 27 prevents entry of foreign material past the bottom of the shaft into the interior of the extension 22.

The assembly of the extension 22 on the handpiece housing 13 and the location of the bearing 16 and shaft 15, as well as the remaining components of the handpiece, can be conventional and requires no further comment.

A family of different blades can be used with a given chuck as long as the mounting portions 123 of all the blades conform to the dimensions of the chuck slot 55 and locking spindle 105 therein. For example, blades may differ in thickness, even in the mounting portion 123, as long as the blade thickness in the mounting portion 123 does not exceed the effective height of the slot 55. In one chuck embodying the invention, blade thickness was in the range of 0.025 inch to 0.050 inch. The recess 83 in the bottom member 51 is preferably deep enough to allow the ramps 93 to be pushed down flush with the top 87 of the shoe cover 86 and the top face 80 of the bottom member 51, i.e. with the bottom of the slot 55.

Further, blades may differ in plan, as to both shape and size in their portions outside the chuck, but with their mounting portions 123 being substantially the same. A blade 12 is fixed in the chuck as follows. The mounting portion 123 of the blade is pushed rearward into the chuck slot 55.

Initial entry of the blade into the chuck slot 55 is made easy by the fact that the first entering portion of the blade, namely the nose 120 is small in height and width compared to the chuck slot 55 which it is to enter. Thus, the nose 120 initially guides the blade 12 easily into the slot 55. Thereafter, the wider rear end 125 of the blade 12 enters the slot 55. This entry is aided by the rounded corners 128 at the rear end 125 of the blade and by the beveled edges 65 at the front end of the slot 55.

Rearward travel of the blade 12 is positively stopped when the blade is only partway (here about halfway) into the chuck, due to collision of the rear end of the nose 120 with the locking segment 109 of the spindle 105 (as seen in FIG. 5A). The locking segment 109 is of diameter greater than the width of the blade mouth 131 and so positively blocks further entry of the blade 12 into the chuck 11. In this position, the blade 12 is quite loose in the chuck 11, and can pivot with respect to the chuck horizontally and vertically (can yaw and pitch). By far the greater portion of the mass of the blade 12 is outside the chuck. The blade 12 very easily falls out of the chuck 11 in normal handling of the handpiece 10, if by operator error the blade is left in its FIG. 5A position. Thus it will be obvious to the operator handling the handpiece that the blade 12 is not chucked, and that complete chucking will require further action by the operator. The blade 12 would normally fall out of its FIG. 5A position in the chuck in normal handling before the handpiece 10 is positioned for use at a surgical site and hence before it is likely that the trigger T would be pulled by the operator. If the trigger T (FIG. 2) is pulled accidentally with the blade 12 in its FIG. 5A position, the resulting motion of the chuck will tend simply to cause the blade to fall out of the chuck and not cause the chuck to throw the blade.

To insert the blade 12 beyond its FIG. 5A position, the operator must depress the spindle 105, from its FIG. 4A position, by downward finger or thumb pressure on the top of the head 106, preferably downward beyond its FIG. 4 position so that the top of the locking segment 109 is flush with or somewhat below the top wall 87 of the shoe cover 86. In this way, the wide locking segment 109 is out of the way of the nose 120 of the blade. The mouth 131 is wide enough to accept the unlocking segment 108 of the spindle, allowing the blade to be pushed to its FIG. 5C position. The distance the blade travels from its FIG. 5A position to its FIG. 5C position is small and is approximately the diameter of the locking segment 109.

If the operator accidentally releases the locking spindle 105 at this time, the spring 114 will immediately raise the locking spindle 105 up through its FIG. 4 position to its uppermost FIG. 4A position, causing the locking segment 109 to lodge in the rear circular part 133 of the slit 127 as shown in FIG. 5C. This positively locks the blade 12 in the chuck 11 and positively prevents any inadvertent release of the blade 12 from the chuck 11 despite actuation of the handpiece 10, violent jerking of the handpiece 10, etc. Thus, by its very short travel from its FIG. 5A position to its FIG. 5C position, the blade 12 is taken from a condition where it will fall freely out of the chuck 11 without harm, to a condition in which it is positively locked within the chuck. The FIG. 5C position may thus be termed a safety, or safety locking position because the blade cannot be accidentally removed from the chuck although it is not yet in a position of use within the chuck. The blade may thus be said to have a safety locking portion comprising the slit part 133. In the FIG. 5C position, the blade can pitch freely up and down with respect to the chuck, which will make apparent to an operator that the blade 12 is still not fully chucked.

Normally the operator maintains the locking spindle head 106 depressed below its FIG. 4 position all during insertion of the blade 12 into the chuck. Thus, the blade would normally pass through its FIGS. 5A, 5B and 5D position into its fully installed FIG. 5E position without the above discussed stopping in its FIG. 5C position.

More particularly, then, continued insertion of the blade 12 into the chuck 11 with the locking spindle head 106 fully depressed, allows the blade to continue through its FIG. 5D position wherein the unlocking segment 108 passes through the neck 134 as shown in FIG. 5D and into the front circular part 132 of the slit 127, bringing the blade to its fully installed position of FIG. 5E. Collision of the blade rear end 125 with the depending pins 63 clearly tells the operator that the blade 12 is fully inserted in the chuck 11 and the operator can release the locking spindle head 106.

Even if the operator prematurely releases the locking spindle head 106, with the blade 12 in its FIG. 5D position, the top of the locking segment 109 of the spindle 105 will simply ride on the underside of the blade 12 until the locking spindle enters the front circular part 132 of the slit 127, whereupon the spring 114 drives the locking spindle 105 upward and thereby raise the spindle locking segment 109 up into the circular front part 132 of the slit 127, as shown in FIG. 5E. The blade is thus fully installed within the chuck.

In its fully installed or final locking FIG. 5E position, the blade rear end 125 firmly abuts the depending pins 63 of the chuck top member 50 to positively prevent further entry into the chuck while eliminating any significant rearward stress on the locking spindle 105 during cutting. The blade may thus be said to have a final locking portion comprising the slit part 132 side edges 124 of the blade abut substantially more than half the entire length of the side walls 62 of the groove 55, which positively prevents significant yawing of the blade with respect to the chuck during operation and without placing high unit pressures on blade edges 124.

Figure 4C:
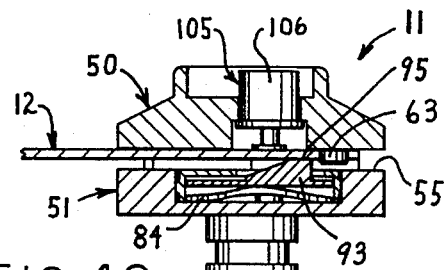
FIGS. 4B and 4C are enlarged central cross-sectional views substantially taken on the line 4B—4B of FIG. 5D and line 4C—4C of FIG. 5E respectively.
Figure 4B:
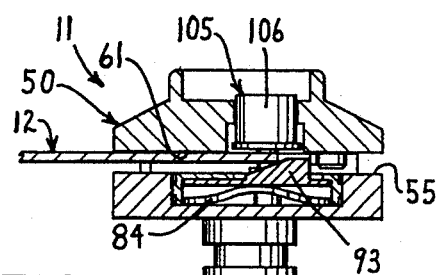
Figure 8:
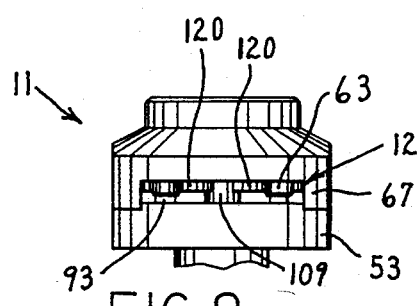
FIG. 8 is an enlarged rear elevational view of the chuck substantially as taken on the line 8—8 of FIG. 3, with a blade inserted.

The rear end 125 of the rearward moving blade 12, after passing its safety position of FIG. 5C, rides up the slopes 194 of the ramps 193 (FIGS. 4B and 5D) and is thereby pushed up against the top 61 of the slot 55 of the chuck 11. The rear end 125 of the blade continues further rearwardly along the slopes 94 of the ramps 93, depressing the ramps 93 against the force of the wave spring 84, as seen in the transition from FIG. 4B to FIG. 4C. Further insertion of the blade 12 causes it to cover the tops 95 of the ramps 93 (FIGS. 4C and 5E). The wave spring 84 acts strongly enough through the tops 95 of the ramps 93 to firmly hold the parts of the blade 12 to the rear (the nose 120 and rear end 125) and front thereof, and hence the entire chucked mounting portion 123 of the blade 12, flat against the top 61 of the slot 55 of the chuck 11 (FIGS. 4A, 4C and 8). The thus fully chucked blade 12 thus strongly resists any tendency to pitch, with respect to the chuck 11, during use.

Forward withdrawal of the blade 12 from the chuck 11, after use, is by a reversal of the above steps required to chuck the blade. More particularly and briefly stated, the operator applies his thumb or forefinger to the top of the spindle head 106 to push same from its FIG. 4A position downward past its FIG. 4 position to disengage the locking portion 109 from the spindle from the blade 12. The operator can simply then pull the blade 12 forward out of the chuck 11. Thereafter, the operator can release the spindle 105, allowing it to rise back to its FIG. 4A position.

The chuck 11 is able to chuck blades of a range of thicknesses, for example, at least twice as thick as the blade 12 here shown, and if desired a somewhat thinner blade than the blade 12 here shown. For example, one set of blades constructed according to the invention ranged in thickness from about 0.025 inch to about 0.05 inch with the height of the slot 55 being about 0.055 inch.

Figure 3:
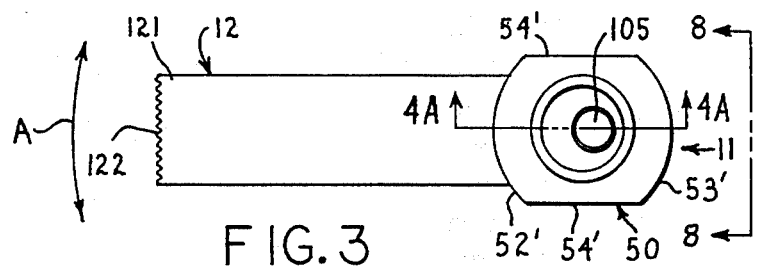
FIG. 3 is a top view of the chuck and blade structure of FIG. 2.

With a blade 12 installed in the chuck 11, the handpiece 10 can be actuated conventionally to produce the desired oscillating or sagittal motion of the chuck and hence of the blade teeth, such motion being schematically indicated by the arrow A in FIG. 3. In the embodiment schematically shown in FIG. 2, pressing of the trigger T by the operator causes the switch S to apply power from the power source P to the motor M to rotate the shaft 15 and orbit the eccentric drive pin 20 and thereby laterally swing the link 35 back and forth horizontally to cause a small arcuate oscillation in a horizontal plane of the chuck 11 and blade 12.

The lateral swing of the saw blade 12 is typically in the range of 3 to 6 degrees, for example, 4.5 degrees.

Thus, the invention, as can be seen from the foregoing, provides several advantageous results. These include the following.

The chuck 11 has only a single slot 55 opening to the outside but yet can accommodate blades of differing thickness and still provide the ability to make precision cuts, such as those encountered in total knee arthroplasty.

Further, only a relatively low spring force (of the spring 114), urging the blade 12 against the "roof" (central flat 61) of the chuck, is required to eliminate excessive vibration and "play" of the blade with respect to the chuck while cutting and to allow the user of the handpiece to maintain precise control of the blade during cutting. Further, such spring force (of spring 114) is low enough that any resulting frictional forces tending to resist insertion or retraction of the blade with respect to the chuck can be readily overcome by hand.

Further, in the safety lock position (for example, see FIG. 5C) the blade 12 is positively locked in the chuck 11, although not yet fully inserted thereinto. If the blade has not been inserted far enough into the chuck to be positively locked in its FIG. 5C safety lock position, then the blade is still so loose in the chuck that it is immediately apparent that it is not chucked and it is not ready for use. Indeed, in that condition, if the chuck is angled downward, the blade will simply fall freely from it. Prior to reaching the safety lock position of FIG. 5C, there is no intermediate range of insertion in which the blade is frictionally retained sufficient to mislead a user into thinking that the blade is fully inserted or locked in the chuck or in a position of use. Well before the blade has been inserted far enough into the chuck to be in its FIG. 5E position of use, it must already have been positively locked (as in FIG. 5C) against accidental dislodgement from the chuck. The foregoing avoids a blade being forcibly thrown from the chuck upon triggering of the handpiece following a careless partial insertion of the blade.

In addition, the relative location of the locking spindle 105 and ramps 93 and the relative location of the spindle engaging rear end of the nose 120 with respect to the ramp engaging rear edge 125 of the blade prevents any significant gripping of the blade by the chuck until the blade has been inserted enough as to be in or past its FIG. 5C safety lock position.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A saw blade of the kind usable in tools including surgical oscillating and sagittal saws, said blade comprising:
   first and second edge portions;
   cutting means along said first edge portion of the blade to effect cutting upon cutting movement of the blade;
   mounting means defining said second edge portion of said blade, said mounting means comprising safety and final locking means for removably interlocking the blade with a chuck, said final locking means being distinct from said safety locking means, in which said safety and final locking means both are part of slit means opening through the rear end of the blade, said slit means having at least one notch intermediate its ends for locking said blade against unintended removal from said chuck, said notch defining said final locking means.

2. The blade of claim 1 in which said safety and final locking means comprise respective rear and front notches spaced along said slit means for sequentially receiving a projection on the chuck, one of said rear and front notches being said at least one notch.

3. A saw blade useable in slotted chuck tools particularly surgical oscillating and sagittal saws, said blade comprising:
   first and second edge portions;
   cutting means along said first edge portion for effecting cutting upon cutting movement of the blade;
   mounting means at said second edge portion of the blade for linear insertion into a chuck slot, said mounting means defining safety locking means interengageable in a chuck slot for positively locking the blade therein upon only a partial linear insertion of the blade into such a chuck slot, said mounting means further defining final locking means interengageable in a chuck slot for positively locking the blade therein upon completion of linear insertion of the blade into such a chuck slot.

4. The blade of claim 3 in which said mounting means include a slit in said second edge portion and having an open end, said safety locking means and final locking means being located in sequence on said slit with said final locking means being further from said open end of said slit than said safety locking means.

5. The blade of claim 4 in which said final locking means comprises a notch in the blade, said notch opening into said slit.

6. The blade of claim 4 in which said safety locking means comprises a notch in said blade, said notch opening into said slit.

7. The blade on claim 3 in which said locking safety and final means on said blade comprises a rear opening slit, said slit being substantially dumbbell shaped, having an opposed rear pair of notches on opposite sides of the slit adjacent to and open to the open rear end of said slit and further having a front pair of opposed notches adjacent the forward end of the slit, the rear pair of notches and front pair of notches respectively defining the safety and final locking means of said blade.

8. The blade of claim 7 including a narrow nose protruding rearward from the rear end of said blade, said slit opening rearward through said nose, means on the rear end of said blade and beside said nose for determining the full rearward position of said blade in a chuck by abutting a projection into a blade receiving slot of a chuck.

9. The blade of claim 3 in which said blade has means defining an axis along which the blade is movable for insertion of the blade into a chuck slot, said mounting means further including nose end means for leading insertion of the blade into a chuck slot, said nose end means and safety locking means and final locking means being aligned in sequence along said insertion axis of the blade.

10. The blade of claim 3 in which a said final locking means on said blade comprises a rear opening slit, said slit having a notch in a side thereof for positively locking said blade with respect to a locking means in a chuck slot and thereby for positively locking said blade against unintended removal from a chuck.

11. A saw blade of the kind usable in tools including surgical oscillating and sagittal saws, said blade comprising:

first and second edge portions;

cutting means along said first edge portion of the blade to effect cutting upon cutting movement of the blade;

mounting means defining said second edge portion of said blade, said mounting means comprising safety and final locking means for removably interlocking the blade with a chuck, said final locking means being distinct from said safety locking means, in which said mounting means includes a rear end of said blade and a nose extending rearward from said rear end of said blade, said locking means comprising a slit laterally dividing said nose into laterally opposed tines and extending forward from said nose and past said rear end, said tines being narrow compared to the width of said blade forward of said blade rear end, said slit having spaced rear and front notches located respectively to the rear and front of said blade rear end for sequentially receiving a projection on the chuck therebetween and for respectively defining said safety and final locking means.

12. A cutting blade useable in powered surgical tools, particularly oscillating and sagittal saws having slotted chucks, the blade comprising:

an elongate blade member having length, width and thickness dimensions;

means at one length end of said blade member for cutting;

mounting means at the other length end of said blade member for insertion in a slot in a chuck, said mounting means including nose means for leading said mounting means into a chuck slot, said mounting means including safety locking means insertable in a chuck slot for positively locking said blade member with respect to a chuck upon insertion into suck chuck slot, said mounting means further including final locking means engageable in a chuck slot for positively locking said blade member with respect to a chuck upon insertion thereinto, said nose means and safety locking means and final locking means being located in sequence along and adjacent a central length axis of said blade member.

13. The blade of claim 12 in which said blade member include a slit and said safety locking means defines a first widening of said slit, said final locking means defining a second widening of said slit spaced from said nose means by said safety locking means.

14. As follows the blade of claim 13 in which said first widening of said slit is defined by opposed notches in opposite sides of said slit, said second widening of said slit being defined by opposed second notches in opposite edges of said slit, said slit extending along a length dimension of said blade, said notches extending in a width direction of said blade transverse to said length direction, said nose means comprising parallel tines extending in the length direction of the blade substantially parallel to each other and spaced apart in the width direction of the blade by a slit, said tines defining said nose, said nose having end means for guiding said blade into a chuck slot, said nose have side edge means and a convergent free end for guiding said blade between a pair of projections in a chuck slot, said nose side edge means meeting and being flanked by stop edge means extending therefrom transverse to the length dimension of said blade for engaging projections in a chuck slot and thereby for stopping positively lengthwise insertion of said blade into a chuck slot, said stop edge means being located along a line between said first and second widenings measured in the length direction of said blade.

15. The blade of claim 12 in which said blade member includes a slit, said blade member nose means including a pair of tines, spaced across said slit, said slit extending along said length axis of said blade member.

16. The blade of claim 12 in which said mounting means include edge means for engagement by a projection in a chuck slot, said edge means extending lengthwise of said blade member from said nose means along said safety locking means and final locking means, said safety locking means and final locking means comprising notches indenting said edge means and opening therethrough in the width direction of said blade member.

17. A saw blade useable in surgical tools including surgical oscillating and sagittal saws, said blade comprising:

first, and second edge portions;

cutting means along said first edge portion of the blade to effect cutting upon cutting movement of the blade;

mounting means defining said second edge portion of said blade, said mounting means comprising laterally spaced side edges said blade having a length axis spaced laterally between said side edges and extending through said first and second edge portions, said mounting means comprising a mounting edge spaced laterally between said length axis and one of said side edges, said mounting edge comprising:

a safety peninsula protruding laterally toward said length axis, a locking peninsula protruding laterally toward said length axis and spaced generally along said length axis between said safety peninsula and said first edge portion, a first bay longitudinally connecting said peninsulas and opening toward said length axis at a greater lateral distance therefrom than are said peninsulas, and a second bay extending longitudinally from said locking peninsula towards said first edge portion and opening toward said length axis.

18. The apparatus of claim 17 in which said mounting means includes a second mounting edge comprising a substantial mirror image of said first mentioned mounting edge and spaced laterally therefrom across said length axis, aid first and second mounting edges defining therebetween a slit in said second edge portion, said slit having an open end.

19. The apparatus of claim 18 in which the safety peninsulas of said first and second mounting edges are laterally opposed and spaced, said locking peninsulas of said first and second mounting edges being laterally opposed and spaced, said slit being laterally wider at said first and second bays than at said opposed safety peninsulas and locking peninsulas.

20. The apparatus of claim 17 in which said safety peninsula defines safety lock means interengageable in a chuck slot for positively locking the blade therein upon only a partial linear insertion of the blade into such a chuck slot, said lock peninsula defining a final locking means interengageable in a chuck slot for positively locking the blade therein upon completion of linear insertion of the blade into such a chuck slot.

21. In a surgical handpiece, cutting apparatus comprising:
- a blade having cutting means at one edge portion thereof;
- a chuck including a blade receiving slot for longitudinally slidably receiving said blade therein;
- cooperating mounting means in said chuck slot and on said blade, said chuck slot being sized in thickness to receive blades of a range of thicknesses, said slot having opposed walls, said walls being adapted to face the width/length faces of the blade, means defining a resiliently backed member urged from one of said walls toward the other and extending into said slot for pressing said blade against the other wall and thereby for firmly locating, in said slot, blades of various thicknesses less than the thickness of the slot.

22. The apparatus of claim 21 in which said blade has a nose extending away from said one edge portion and located for leading said blade into said chuck slot, said resiliently backed member of said chuck having laterally spaced ramps engageable with a portion of said blade longitudinally between said nose and said cutting means to carry out said pressing of said blade against said other wall, said nose being laterally narrower than the space laterally between said ramps for location between said ramps up insertion of said blade into said chuck slot.

23. The apparatus of claim 22 in which said chuck includes projections into said slot in the thickness direction thereof, said projections being located adjacent respective said ramps, said ramps being interposed between said projections and said cutting means, said nose being insertable laterally between said projections during final insertion of said blade into said chuck slot, said blade having shoulders laterally outwardly extending beyond said nose and engageable with said projections to stop insertion of said blade further into said slot, said ramps pressing said blade at its shoulders toward said other wall of said slot.

24. The apparatus of claim 23 in which said projections lie at least close to lateral side edges of said chuck slot, said blade being free of any portion receivable laterally between a given projection and the adjacent side edge of said slot.

25. A surgical cutting blade for releasable mounting on a powered surgical handpiece chuck, the blade comprising:
- cutting means responsive to powered movement of the blade for cutting patient tissue and the like;
- mounting means remote from said cutting means for removable mounting said blade on the chuck of a powered surgical handpiece, said mounting means comprising a substantially parallel pair of side edge means snugly and slidably receivable between sidewalls of a chuck slot for preventing yawing movement of the blade with respect to a chuck during powered movement of the blade, shoulder edge means extending transversely inward toward each other from respective ones of said side edge means for stopping insertion of said blade into a surgical handpiece chuck slot by abutting insertion stop means in a chuck slot, fork means protruding centrally from between said shoulder edge means away from and in a direction substantially parallel to said side edge means and thus away from said cutting means for initially guiding the mounting means of the blade into a surgical handpiece chuck slot prior to entry of said shoulder edge means and side edge means thereinto, said blade being laterally narrower at said fork means than between said side edge means, said fork means comprising a free end remote from said shoulder edge means and a slit opening at said free end and extending forward into said fork means and extending parallel to said fork means and side edge means, said slit being longer than said fork means and extending forward past said shoulder edge means into a portion of said blade between said shoulder edge means and cutting means, said slit being for slidably receiving a shank of a surgical handpiece chuck during insertion of said blade thereinto, said slit having an outboard portion dividing said fork means into a pair of substantially parallel tines, means defining a hole through said blade widening a portion of said slit for receiving an enlarged head of a shank of a surgical handpiece chuck and therewith for locking said blade in a surgical handpiece chuck slot for powered cutting, said hole being spaced inboard from said shoulder edge means and being spaced transversely between said side edge means.

26. The apparatus of claim 25 which in the side edge means each join a respective shoulder at a respective portion tapered to facilitate insertion of said blade into a surgical handpiece chuck slot.

27. The apparatus of claim 25 in which the free ends of said tines are tapered to facilitate entry of said tines into a powered surgical handpiece chuck slot.

28. In a surgical handpiece, a cutting apparatus comprising:
- a chuck including a blade receiving slot for longitudinally slidably receiving a blade therein, said chuck slot having opposed sidewalls, insertion stop means fixed within said chuck slot, said chuck slot having a rear end and a front opening to receive a blade, said insertion stop means being spaced closer to said slot rear end than said slot front end, said chuck having locking means including a shank bearing an enlarged head and shiftable thicknesswise of said slot for alternatively placing said shank and said enlarged head in said slot;
- a blade including cutting means responsive to powered movement for cutting patient tissue and the like, mounting means remote from said cutting means for removable mounting of said blade in said chuck, said mounting means comprising a substantially parallel pair of side edge means snugly and slidably receivable between said side walls of said chuck slot for preventing yawing movement of said blade with respect to the chuck during powered movement of said blade, shoulder edge means extending transversely inward generally toward each other from respective side edge means for stopping insertion of said blade into said chuck slot by abutting said insertion stop means in said chuck slot, fork means protruding centrally from between said shoulder means and rearwardly away from and in a direction substantially parallel to said side edge means and thus rearwardly away from said cutting edge means for initially guiding said mounting means of said blade into said chuck slot prior to entry of said shoulder means and side edge means into said chuck slot, said blade being laterally narrower at said fork means than between said side edge means thereof, said fork means comprising a free end remote from said shoulder means and a slit opening at said free end and extending forward into said fork means, said slit extending parallel to said fork means and side edge means, said slit being longer than said fork means and extending forward past said shoulders into a portion of said blade between said shoulders and cutting means, said slit being for slidably receiving said shank of said chuck during insertion of said blade thereinto, said slit having an outboard portion dividing said fork means into a pair of substantially parallel tines, means defining a hole through said blade and widening a portion of said slit and of diameter greater than the minimum width of said slit for receiving said enlarged head of said shank of said chuck and therewith for locking said blade in said chuck slot for powered cutting, said hole being spaced inboard from said shoulders and being spaced transversely between said side edge means.

29. A surgical saw blade, for a powered surgical handpiece chuck, which chuck has an elongate forwardly opening slot transversely wide between its sides but of thin cross-section and has stop pins offset rearward near the rear end of the slot remote from the open slot front end and extending thicknesswise of the slot and spaced widthwise of the slot on opposite sides of a longitudinal center line of the slot, and has a lock member extending thicknesswise of said slot and located substantially along the central longitudinal axis of the slot and spaced forward from said stop pins and rearward from the open forward slot end wherein relatively thick and thin parts of the lock member are alternatively axially insertable across the thickness of the chuck slot, and has ramps resiliently urged thicknesswise up into said chuck slot through a slot floor and toward a slot roof and spaced widthwise of the slot on opposite sides of the slot longitudinal centerline forward of respective stop pins and rearward of the forward open end of the slot, said blade comprising:

(1) a planar plate-like body of length greater than width greater than thickness, (2) cutting means at a forward end portion of said blade body and movable by a surgical handpiece chuck for surgical cutting while projecting forward from a chuck slot;

(3) mounting means at a rearward end portion of said blade body for rearwardly sliding lengthwise and into a chuck slot forward end, said blade end portions being spaced longitudinally of the blade from each other, said mounting means comprising:

(a) means defining substantially parallel first and second side edges spaced widthwise of said blade for longitudinally slidable engagement snugly between sides of a chuck slot for guiding insertion into and preventing yaw movement of the blade in a chuck slot;

(b) insertion blocking means defining a first rear facing insertion blocking shoulder extending widthwise of the blade inboard from said first side edge for abutting a corresponding stop pin offset rearward in a chuck slot and therewith for positively blocking further insertion of said blade shoulder into a chuck slot;

(c) means defining a mounting edge extending in said blade forward past said first insertion blocking shoulder and laterally spaced between a central longitudinal axis of said blade and said first side edge, said mounting edge comprising a first locking peninsula means spaced at a first distance from said blade central longitudinal axis in a direction widthwise of said blade for blocking forward and rearward blade movement past a chuck lock member thick part but allowing such blade movement past a chuck lock member thin part, said mounting edge further comprising a first locking bay having a boundary edge spaced widthwise from said central longitudinal axis of said blade at a distance widthwise of said blade farther than said locking peninsula for receiving a chuck lock member thick part, such that said locking bay extends farther widthwise of said blade from said blade central longitudinal axis than does said locking peninsula, said locking bay being spaced forward from said insertion blocking shoulder;

(d) first edge means connecting the inboard end of said first shoulder to a rearward end of said mounting edge;

(e) means defining blade body top and bottom faces bounded in part by said side edges and shoulder and mounting edge for pressing of said blade body bottom face by a chuck ramp and therewith urging said blade body top face firmly against a chuck slot roof;

(f) second edge means extending from a forward end of said locking bay boundary edge at least initially away from said central longitudinal axis of the blade and eventually connecting to said second side edge of the blade, said second edge means being on the opposite side of said blade longitudinal center line from said locking bay and locking peninsula and first shoulder and first edge means and first side edge of said blade, said second edge means being spaced from said blade central longitudinal axis at least as far as are said locking bay and locking peninsula for allowing (i) rearward movement of said blade body insertion blocking shoulder into a forward opening chuck slot toward a ramp and stop pin therein, then (ii) further rearward movement of said shoulder past a chuck lock member, then (iii) further rearward movement of said shoulder onto a chuck slot ramp and then (iv) further rearward movement of said shoulder into abutment with a chuck stop pin.

30. The apparatus of claim 29 in which said second side edge means defines a second locking peninsula and locking bay opposed widthwise of said blade, symmetrically across a longitudinal slit in said blade body, from said first locking peninsula and locking bay.

31. The apparatus of claim 30 in which said second edge means defines a second shoulder extending widthwise of said blade inboard from the second said side edge, said first and second edge means defining respective first and second tines extending rearward from said first and second shoulders, said slit extending rearward between said tines.

32. The apparatus of claim 31 in which said slit is widened by a safety opening defined by opposed safety bays in said tines, as well as by a locking space opening by said opposing first and second locking bays.

33. In a powered surgical handpiece, a cutting apparatus comprising:

a chuck mounted on and moved by the handpiece, the chuck having an elongate forwardly opening slot of transversely wide but thin cross section, stop members offset rearward near the rear end of said slot remote from the open slot front end and extending thicknesswise of the slot and spaced widthwise of said slot on opposite sides of a longitudinal center line of said slot, said stop members being fixed in said slot, a lock member extending thicknesswise of said slot and located substantially along said central longitudinal axis of said slot and spaced between said stop members and the open forward end of said slot, said lock member having relatively thick and thin parts alternatively axially insertable across the thickness of said chuck slot, ramps resiliently urged thicknesswise up into said chuck slot through a slot floor and toward a slot roof and spaced widthwise of said chuck slot on opposite sides of said chuck slot longitudinal center line forward of respective ones of said stop members and rearward of the forward open end of said slot;

a blade having a planar plate-like body of length greater than width greater than thickness, cutting means adjacent a forward end portion of said blade body and movable by said chuck for surgical cutting while projecting forward from said chuck slot, mounting means adjacent a rearward end portion of said blade body for rearwardly sliding lengthwise into said chuck slot forward end, said end portions being spaced longitudinally of said blade from each other, said mounting means comprising means defining a substantially parallel first and second side edges spaced widthwise of said blade for longitudinally slidable engagement snugly between opposed sides of said chuck slot for guiding insertion into and preventing yaw movement of the blade in said chuck slot, means defining a first rear facing insertion blocking shoulder extending widthwise of said blade inboard from said first side edge for abutting a corresponding said stop member, the last mentioned stop member being offset rearward in said chuck slot and therewith for positively blocking further insertion of said blade into said chuck slot, means defining a mounting edge extending on said blade forward past said first insertion blocking shoulder and laterally spaced between a central longitudinal axis of said blade and said first side edge, said mounting edge comprising a first locking peninsula spaced at a first distance from said blade central longitudinal axis in a direction widthwise of said blade for blocking forward and rearward blade movement past said chuck lock member thick part and not said thin part thereof, said mounting edge further comprising a first locking bay having a boundary edge spaced widthwise from said central longitudinal axis of said blade at a distance widthwise of said blade farther than said locking peninsula for receiving said chuck lock member thick part, such that said locking bay extends farther widthwise of said blade from said blade central longitudinal axis than does said locking peninsula, said locking bay being spaced forward from said first shoulder, first edge means connecting the inboard edge of said first shoulder to a rearward end of said mounting edge, means defining blade body top and bottom faces bounded in part by said side edges and shoulder and mounting edge for pressing of said blade body bottom face by said chuck ramp and therewith urging said blade body top face firmly against said chuck slot roof, second edge means extending from a forward end of said locking bay boundary edge at least initially away from said central longitudinal axis of said blade and eventually connecting to the second said side edge of said blade, said second edge means being on the opposite side of said blade longitudinal center line from said locking bay and locking peninsula and first shoulder and first edge means and first side edge of said blade, said second edge means being spaced from said blade central longitudinal axis at least as far as said locking bay and locking peninsula for allowing (i) rearward movement of said blade shoulder into said forward opening chuck slot toward a corresponding said ramp and stop member therein, then (ii) further rearward movement of said shoulder past said chuck lock member, then (iii) further rearward movement of said shoulder onto said corresponding ramp and then (iv) further rearward movement of said shoulder into abutment with said corresponding chuck stop member.

* * * * *

UNITED STATES PATENT AND TRADEMARK OFFICE
CERTIFICATE OF CORRECTION

PATENT NO. : 5 439 472
DATED : August 8, 1995
INVENTOR(S) : James A. EVANS, et al.

It is certified that error appears in the above-indentified patent and that said Letters Patent is hereby corrected as shown below:

Column 14, line 36; delete "locking".
line 37; after "final" insert ---locking---.
Column 15, line 37; change "suck" to ---such---.
line 45; change "include" to ---includes---.
line 49; change "As follows the" to ---The---.
line 59; change "a" to ---said---.
line 60; change "said" (first occurrence) to ---a---.
Column 16, line 20; delete ",".
line 26; after "edges" insert ",".
line 51; change "aid" to ---said---.
Column 17, line 27; change "up" to ---upon---.
Column 18, line 24; change "which in" to ---in which---.

Signed and Sealed this

Ninth Day of January, 1996

*Attest:*

BRUCE LEHMAN

*Attesting Officer*  *Commissioner of Patents and Trademarks*